United States Patent [19]

Longley et al.

[11] 4,154,955

[45] May 15, 1979

[54] SULFOSUCCINATE ESTER-AMIDES

[75] Inventors: Kermit D. Longley, Park Forest; Anastasios J. Karalis, Chicago, both of Ill.

[73] Assignee: Witco Chemical Corporation, New York, N.Y.

[21] Appl. No.: 845,508

[22] Filed: Oct. 25, 1977

Related U.S. Application Data

[63] Continuation of Ser. No. 535,763, Dec. 23, 1974, abandoned.

[51] Int. Cl.² .................. C07C 143/13; C07D 295/00
[52] U.S. Cl. .................................... 560/151; 252/354; 252/542; 252/545; 260/29.6 R; 544/110
[58] Field of Search .......................... 560/151; 544/110

[56] References Cited

U.S. PATENT DOCUMENTS 4,056,558 11/1977 Sundby ............................... 560/151

*Primary Examiner*—Vivian Garner
*Attorney, Agent, or Firm*—Albert L. Gazzola; Morton Friedman

[57] ABSTRACT

Sulfosuccinate ester-amides in which one carboxyl group of the sulfosuccinate is amidified with an aliphatic non-tertiary amine, for instance, a $C_8$–$C_{12}$ aliphatic amine such as octyl or dodecyl amine, and in which the other carboxyl group of the sulfosuccinate is esterified by reaction with an α-monoepoxide such as propylene oxide, or higher α-monoepoxides, and method of preparation of such sulfosuccinate ester-amides. The said sulfosuccinate ester-amides have utility as surfactants, such as detergents and emulsifiers.

6 Claims, No Drawings

SULFOSUCCINATE ESTER-AMIDES

This is a continuation, of application Ser. No. 535,763, filed 12/23/74, now abandoned.

Our invention relates to the preparation of certain types of novel sulfosuccinate ester-amides at least most of which can be represented by the following formula:

$$R-NX-\underset{\underset{O}{\|}}{C}-\underset{\underset{SO_3M}{|}}{CH}-CH_2-\underset{\underset{O}{\|}}{C}-O-CH_2-\underset{\underset{OH}{|}}{CH}-R^1 \quad (I)$$

where R—NX is the radical of a $C_2$-$C_{20}$, preferably a $C_3$-$C_{18}$ aliphatic non-tertiary monoamine in which X is hydrogen or lower ($C_1$-$C_5$) alkyl; and $R^1$ is alkyl containing from 1 to 18 carbon atoms; with the proviso that the sum of the number of carbon atoms in R—NX— and $$-CH_2-\underset{\underset{OH}{|}}{CH}-R^1$$

is from 7 to 35 and that there is a difference in the number of carbon atoms in R—NX— and $$-CH_2-\underset{\underset{OH}{|}}{CH}-R^1$$

which difference is at least 2 and, better still, at least 4; and M is a cation selected from the group of alkali metals (including ammonium), alkaline earth metals, and organic substituted ammonium or water soluble amines. Most desirably, the difference in the number of carbon atoms between R—NX— and $$-CH_2-\underset{\underset{OH}{|}}{CH}-R^1$$

is from 4 to 14. Again, generally, speaking, the preferred novel compounds of our present invention are those wherein, in the aforesaid formula, R is alkyl containing from 8 to 15 carbon atoms, X is hydrogen, and $R^1$ is methyl and those wherein, in the aforesaid formula, R is alkyl containing from 3 to 5 atoms, X is hydrogen and $R^1$ contains from 6 to 10 carbon atoms.

It is particularly desirable that the novel sulfosuccinate ester-amide compounds of our present invention be marketed and used in the form of the aforementioned types of salts, that is, where M in formula (I) is an alkali metal (which term is here used to mean sodium, potassium, lithium and ammonium), or alkaline earth metals, namely, calcium, magnesium, strontium and barium; or, as noted above, organic substituted ammonium or amines. These latter, which most advantageously are water-soluble lower molecular weight amines, may be selected from a wide group, typical examples of which are dimethylamine; diethylamine; triethylamine; propylamine; monoisopropylamine, diisopropylamine, triisopropylamine, and commercial mixtures of said isopropylamines; butyl amine, amyl amine, monoisopropanolamine, diisopropanolamine, triisopropanolamine and commercial mixtures of said isopropanolamines; ethanolamines such as monoethanolamine, diethanolamine, triethanolamine, and commercial mixtures thereof; polyamines such as aminoethyl ethanolamine, ethylenediamine, diethylenetriamine, hydroxyethyl ethylenediamine, and hexamethylenediamine; hexylamine; cyclohexylamine; dimethylbenzylamine, benzylamine; morpholine; etc. Such salts can be prepared from sodium or potassium salts of the novel sulfosuccinate esteramide compounds of our present invention by known metathesis techniques.

The aforesaid sulfosuccinate ester-amides are characterized by the fact that there is present in the molecules thereof, connected through an ester linkage to one of the carboxyl groups of maleic anhydride, a free hydroxyl group in the α-position resulting from the utilization of an α-epoxide containing at least 3 carbon atoms in the production of the compounds of our invention, and an amide linkage connected through the other one of the carboxyl groups of the maleic anhydride, all as is hereafter described in detail and illustrated by the various disclosed embodiments of our invention. The special combination of radicals in the compounds of our invention results in particular properties which effectively adapt various of the compounds to highly effective utilities in various environments.

In certain cases, the radical R—NX— in formula (I) will be derived from a long chain, for instance a $C_8$-$C_{20}$, aliphatic primary monoamine, and the radical $$-CH_2-\underset{\underset{OH}{|}}{CHR'}$$

in said formula (I) will be derived from an α-epoxide such as propylene oxide or butylene oxide, particularly propylene oxide. However, compounds according to and within the scope of our invention are also obtained where the R—NX— radical of said formula (I) is derived from a $C_2$-$C_5$ aliphatic non-tertiary amine such as ethyl amine, n-propyl amine, isopropyl amine, n-butyl amine, isobutyl amine, n-pentyl amine and isopentyl amine, and the $$-CH_2-\underset{\underset{OH}{|}}{CHR'}$$

radical is derived from a $C_3$-$C_{20}$, particularly a $C_8$-$C_{20}$, α-epoxide such as octylene oxide or dodecylene oxide or styrene oxide.

The aforesaid compounds are useful in various fields where surfactant or wetting-out properties are a desideratum such as, for instance, detergents, emulsifiers, penetrating agents, stabilizing agents, dispersants, emollients, and the like.

Certain sulfosuccinate esters and certain sulfosuccinate amides are known to the art, being disclosed, for instance, in U.S. Pat. Nos. 2,028,091; 2,252,401; 2,316,234; 2,507,030; 2,887,504; 2,976,208; 2,976,209; 2,976,211; 3,002,994; 3,080,280; 3,123,640; 3,123,641; 3,141,905; 3,155,591; 3,404,164; 3,481,973; French Patent of Addition No. 69,516; and C. R. Caryl, Ind. Eng. Chem., 33,731-7 (1941). However, so far as we are aware, there has been no prior suggestion or disclosure of any of the compounds of our invention.

In the preparation of various of the novel compounds of our invention, maleic anhydride is initially reacted with an aliphatic (which term includes cycloaliphatic) primary monoamine in proportions such as to produce predominately the maleic acid monoamide, generally speaking, a mole ratio of 1 to about 1.2 moles of maleic anhydride to 1 mole of the long chain aliphatic primary amine, namely, a reaction product which contains upwards of 90 or 95% of the monoamide. It is generally unnecessary to purify the reaction product to separarte the monoamide but this can be done, if desired, by conventional purification techniques.

In one procedure for the production of the monoamide, particularly where the aliphatic non-tertiary amine reactant with the maleic anhydride is an aliphatic non-tertiary amine, such as, for instance, long chain aliphatic primary amines, said primary amines are initially admixed with the maleic anhydride and reacted, for instance, at about 70° to about 100° C., until the acid number reaches or approximates that of the desired monoamide. To said monoamide is then added the selected α-epoxide in amounts to drive the desired esterification reaction to completion which, in the usual cases, involves the employment of about 0.2 to 0.3 moles excess to effect completion of the reaction in a reasonable length of time. To the resulting ester-amide there is then added slightly more than 1 mole of the bisulfite per mole of maleic anhydride used and the resulting mixture is heated until the reaction is complete. It should be noted that, in the preparation of the novel compounds of our present invention, whether by the preferred procedure described in this paragraph or otherwise in accordance with our invention, it is essential that maleic anhydride be utilized.

The preparation of the intermediate amides, to wit, the N-alkylmaleamic acid, by reaction of the aliphatic non-tertiary monoamines with maleic anhydride is, per se, well known to the art and no novelty is claimed therein. Various methods are known to the art and it is convenient, if desired, to utilize procedures such as are disclosed by Mehta et al, J. Org. Chem. 25,1012 (1960), utilizing an organic solvent reaction medium, such as anhydrous diethylether.

In the preparation of those of the compounds of our invention which are in the form of amine salts, it is sometimes desirable to produce such in substantially anhydrous form, soluble in organic solvents, particularly polar organic solvents such as ethyl alcohol, propyl alcohol, isopropyl alcohol, methyl and ethyl formamides, etc. To this end, for instance, the aforedescribed intermediate ester-amides can be reacted with a solution containing an organic amine, sufficient water to provide a reaction medium and containing dissolved sulfur dioxide to form a sulfite of said organic amine, and a water-miscible alcohol, for instance, methyl alcohol, ethyl alcohol, n-propanol or isopropyl alcohol, whereby to produce a substantially anhydrous organic amine salt of the said sulfosuccinic acid ester-amides. For best results, in carrying out such reaction, for each mol of said intermediate ester-amide, the solution reacted therewith should contain about 1 mole or slightly more of organic amine or amines, and about 1 mol of water containing about 1 mol of sulfur dioxide.

In the preparation of the novel compounds of our invention by the foregoing method, it is important, in order to obtain said compounds, that the sequence of steps noted above be followed, that is, that the maleic acid monoamide of the $C_1$–$C_{20}$ aliphatic non-tertiary amine first be provided or prepared after which the reaction with the α-epoxide is carried out, followed by the reaction with the aqueous bisulfite to introduce the sulfonic group into the molecule. Thus, for instance, if the α-epoxide is first reacted with the maleic anhydride and then with (a) the $C_2$–$C_{20}$ aliphatic non-tertiary amine, followed by the reaction with the aqueous bisulfite, or (b) the aqueous bisulfite followed by the reaction with the $C_2$–$C_{20}$ aliphatic non-tertiary amine, the products of or contemplated by the present invention are not obtained.

In the reaction of the monoamides with the α-epoxides containing at least 3 carbon atoms to produce the intermediate ester-amides which are then converted into the sulfosuccinate ester-amides of our invention, said reaction is especially desirably carried out in the presence of a catalyst, particularly a basic organic material such as, by way of example, tertiary amines such as triethylamine and triisopropylamine; tris dimethylamino methyl phenol; and quaternary ammonium salts such as tetramethyl ammonium hydroxide, tetraethyl ammonium hydroxide, benzyl trimethyl ammonium hydroxide and benzyl triethyl ammonium hydroxide. Inorganic basic catalysts such as sodium hydroxide or potassium hydroxide can be used but are not preferred. The catalysts can be used in variable proportions, generally in the range of 0.1 to 2 or 3%, based on the weight of the monoamide, depending generally on the basicity of the catalyst.

The radicals represented by R—NH— in formula (I) or in the formula R—NX can be straight chain or branch chain and include, by way of illustration, radicals derived from such non-tertiary amines as ethyl amine, n-propyl amine, isopropyl amine, n-butyl amine, isobutyl amine, cyclopropyl amine, cyclobutyl amine, cyclopentyl amine, cyclohexyl amine, n-amyl amine, isoamyl amine, n-hexyl amine, isohexyl amine, 2-ethyl hexyl amine, 2-ethyl octyl amine, n-nonyl amine, isononyl amine, n-decyl amine, isodecyl amine, undecyl amine, n-dodecyl amine, isododecyl amine, tridecyl amine, tetradecyl amine, pentadecyl amine, hexadecyl amine, heptadecyl amine and octadecyl amine, and mixtures thereof as in commercial mixtures of fatty and other non-tertiary amines. The non-tertiary amines include the secondary amines corresponding to the primary amines mentioned above, as, for example, di-n-propyl amine, di-n-butyl amine, etc.

The α-epoxides which are utilized in the preparation of the novel compounds of the present invention and from which the radical

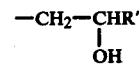

of formula (I) is derived include, by way of illustrative examples, propylene oxide; butylene, pentylene, hexylene, heptylene, octylene, nonylene, decylene, dodecylene, tetradecylene, pentadecylene, hexadecylene and octadecylene oxides, as well as styrene oxide and similar α-epoxides derived from analogous alkenyl benzenes.

Illustrative examples of chemical compounds falling within the scope of our invention are the following:

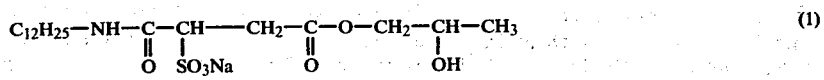

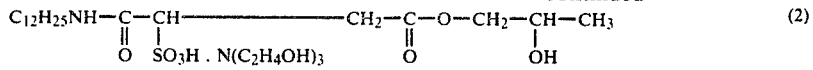  (2)

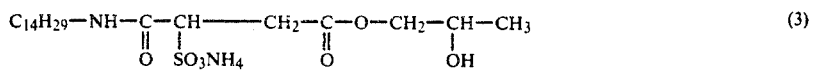  (3)

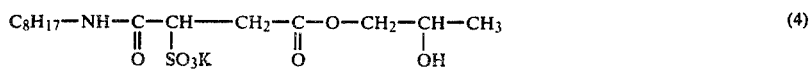  (4)

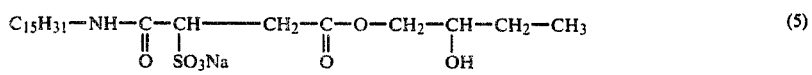  (5)

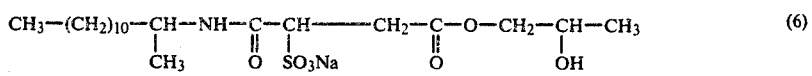  (6)

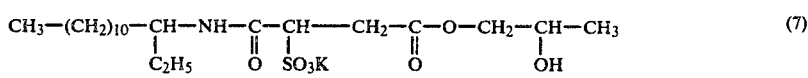  (7)

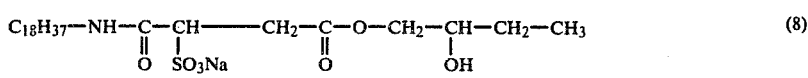  (8)

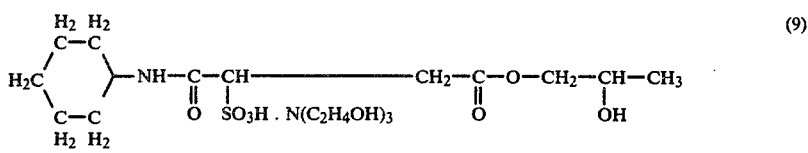  (9)

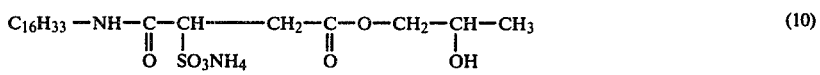  (10)

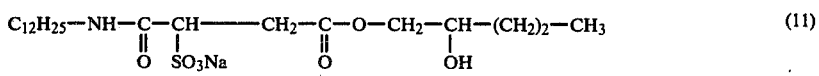  (11)

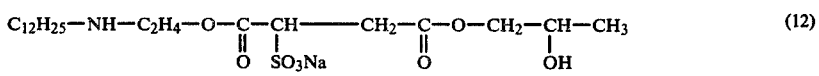  (12)

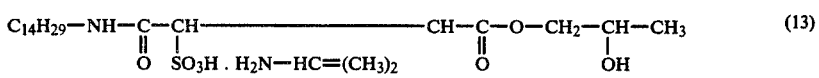  (13)

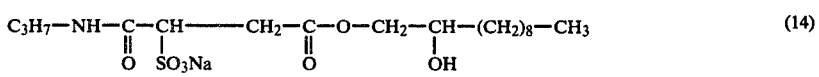  (14)

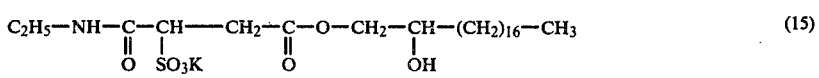  (15)

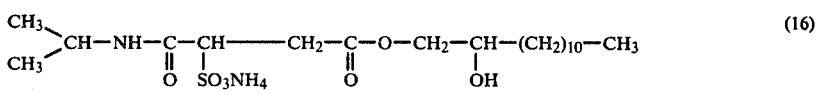  (16)

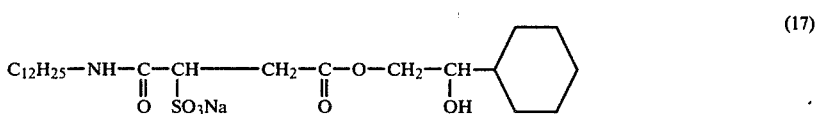  (17)

The following examples are illustrative of the preparation of typical compounds of the present invention. All temperatures recited are in degrees Centigrade.

EXAMPLE I

To 98 g (1 mole) of molten maleic anhydride at 70° there is added 106 g (1.05 moles) of di-n-propyl amine over a period of 1 hour, then stirring an additional 15 minutes at this temperature. To the di n-propyl maleamide so formed there is added 239 g of a $C_{11}$–$C_{14}$ α-olefin epoxide (1.1 mole "Neodox 1114"-Viking Chemical) over a period of 1 ½ hours at 100°–110°, then maintaining at this temperature for an additional 6 hours. At the end of the period, the acid value is 0.027 meq/g. There is then added 327 g (1.1 mole) of 41% sodium bisulfite solution at 90°. The reaction is very rapid and is complete within about 15 minutes. The product, a clear, dark amber viscous solution, clearly soluble in water in all proportions with excellent foaming and lime soap dispersant properties, corresponds to the formula $$\begin{array}{c} CH_3-CH_2-CH_2 \\ \phantom{CH_3-CH_2-CH_2} \diagdown \\ \phantom{CH_3-CH_2-CH_2} N-\underset{\underset{O}{\|}}{C}-\underset{\underset{SO_3Na}{|}}{CH}-\!\!-\!\!-CH_2-\underset{\underset{O}{\|}}{C}-O-(R^1O)H \\ \phantom{CH_3-CH_2-CH_2} \diagup \\ CH_3-CH_2-CH_2 \end{array}$$

(where $R^1O-$ is the radical of said α-olefin epoxide)

EXAMPLE II

To 139 g (0.5 mole) of N-cocomaleamide, having an acid valve of 3.6 meq/g, are added 0.3 g of tris dimethylamino methyl phenol, and then 50 g (0.86 mole) of propylene oxide are added gradually over a period of about 3 hours while the reaction mixture is heated at 100° C., and the reaction mixture is maintained at said temperature for an additional approximately 5 hours or until an acid value is reached of about 0.13 mdq/g. The resulting reaction product is stripped in vacuo, and to it are gradually added, with stirring, 118 g of a 44% aqueous solution of sodium bisulfite (0.5 mole) at 100° C. over a period of about 1 hour, and stirring is continued for an additional ½ hour at a temperature of about 100° C. The final product is a clear, amber liquid completely soluble in water, and corresponds to the formula $$R-HN-\underset{\underset{O}{\|}}{C}-\underset{\underset{SO_3Na}{|}}{CH}-\!\!-\!\!-CH_2-\underset{\underset{O}{\|}}{C}-O-CH_2-\underset{\underset{OH}{|}}{CH}-CH_3$$

(where R—NH— is the radical of coco fatty primary amines)

The product has moderate foaming properties; and it possesses foam stabilizing properties for various surfactants such as alkylaryl sulfonates such as dodecylbenzene sodium sulfonates and dodecylbenzene triethanolamine sulfonates, and long chain aliphatic alcohol sulfates such as lauryl sodium sulfates and lauryl triethanolamine sulfates.

EXAMPLE III

The procedure described in Example I is carried out except that, in place of the di-n-propyl amine, 91 g (about 1.05 moles) of n-amyl amine is used. The sulfosuccinate ester-amide product obtained corresponds to the formula $$C_5H_{11}-NH-\underset{\underset{O}{\|}}{C}-\underset{\underset{SO_3Na}{|}}{CH}-\!\!-\!\!-CH_2-\underset{\underset{O}{\|}}{C}-O-(R^1O)H$$

(where $R^1O-$ is the radical of the said α-olefin epoxide)

EXAMPLE IV

The procedure described in Example II is carried out except that, in place of the propylene oxide, 62 g (0.86 moles) of butylene oxide is used. The sulfosuccinate ester-amide product obtained corresponds to the formula $$R-NH-\underset{\underset{O}{\|}}{C}-\underset{\underset{SO_3Na}{|}}{CH}-\!\!-\!\!-CH_2-\underset{\underset{O}{\|}}{C}-O-CH_2-\underset{\underset{OH}{|}}{CH}-CH_2-CH_3$$

EXAMPLE V

The procedure described in Example II is carried out except that, in place of the N-cocomaleamide, there is used 114 g (0.5 mole) a monoamide of 2-ethylhexyl amine prepared by reacting 2-ethylhexyl amine with maleic anhydride. The sulfosuccinate ester-amide product obtained corresponds to the formula $$R-NH-\underset{\underset{O}{\|}}{C}-\underset{\underset{SO_3Na}{|}}{CH}-\!\!-\!\!-CH_2-\underset{\underset{O}{\|}}{C}-O-CH_2-\underset{\underset{OH}{|}}{CH}-CH_3$$

(where R—NH is the radical of 2-ethylhexyl amine)

EXAMPLE VI

To 400 ml of water are added 34 g of the sulfosuccinate ester-amide surfactant prepared in Example II, 1.25 g of potassium persulfate, 7 g of hydroxyethyl cellulose ("Cellosize WP-09", Union Carbide Corporation), and 1.3 g of sodium bicarbonate. This solution is heated to 70° and to it is added at 70°–75°, in separate streams, over a period of 4 hours, 550 g of vinyl acetate and a solution of 1.25 g of sodium persulfate in 50 ml of water. When the addition is complete, the temperature is raised to 90° for ½ hour. The resulting vinyl acetate latex contains 55% solids and shows no separation after prolonged standing.

We claim:

1. A sulfosuccinate surfactant according to the formula:

$$R-NX-\underset{\underset{O}{\|}}{C}-\underset{\underset{SO_3M}{|}}{CH}-\!\!-\!\!-CH_2-\underset{\underset{O}{\|}}{C}-O-CH_2-\underset{\underset{OH}{|}}{CH}-R^1$$

Where R—NX— is the radical of a $C_2$–$C_{20}$ aliphatic non-tertiary monoamine in which X is hydrogen or lower alkyl; and wherein $R^1$ is selected from the class consisting of alkyl containing from 1 to 18 carbon atoms and phenyl with the proviso that the sum of the number of carbons in R—NX and $$-CH_2-\underset{\underset{OH}{|}}{CH}-R^1$$

is from 7 to 35 and that there is a difference in the number of carbon atoms in R—NX— and $$-CH_2-\underset{\underset{OH}{|}}{CH}-R^1$$

which difference is at least 2 and M is a cation selected from the group of alkali metals, ammonium, alkaline earth metals and water soluble amines.

2. A surfactant according to claim 1, in which the difference in the number of carbon atoms between R—NX— and $$-CH_2-\underset{\underset{OH}{|}}{CH}-R^1$$

is from 4 to 14.

3. A surfactant according to claim 1, in which R is alkyl containing from 8 to 15 carbon atoms, X is hydrogen, and $R^1$ is methyl.

4. A surfactant according to claim 3, in which R is a straight chain alkyl.

5. A surfactant according to claim 1, in which R is alkyl having from 3 to 18 carbon atoms and is a branch chain alkyl.

6. A surfactant according to claim 1, in which R is $C_2$-$C_5$ alkyl and $R^1$ is alkyl containing from 1 to 18 carbon atoms.

* * * * *